United States Patent [19]

Krishnan et al.

[11] Patent Number: 4,958,020
[45] Date of Patent: Sep. 18, 1990

[54] PROCESS FOR PRODUCING BETA-LACTAMASE INHIBITOR

[75] Inventors: Raghavan Krishnan, Suffern; Jesse Gamble, Spring Valley, both of N.Y.; David Blum, Saddle River, N.J.; William V. Curran, Pearl River, N.Y.; Ving J. Lee, Monsey, N.Y.; Ransom B. Conrow, Pearl River, N.Y.

[73] Assignee: American Cyanamid Company, Stamford, Conn.

[21] Appl. No.: 350,966

[22] Filed: May 12, 1989

[51] Int. Cl.$^5$ .................. C07D 499/00; A61K 31/425
[52] U.S. Cl. .................... 540/310; 514/192; 514/195; 210/767; 210/774
[58] Field of Search ............... 514/192, 195; 540/310; 210/767, 774

[56] References Cited

U.S. PATENT DOCUMENTS

| | | | |
|---|---|---|---|
| 4,496,484 | 1/1985 | Micetich | 540/310 |
| 4,529,592 | 7/1985 | Micetich | 540/310 |
| 4,562,073 | 12/1985 | Micetich | 540/310 |
| 4,668,514 | 5/1987 | Micetich | 540/310 |

FOREIGN PATENT DOCUMENTS

| | | | |
|---|---|---|---|
| 61-126087 | 6/1986 | Japan | 540/310 |
| 63-112588 | 5/1988 | Japan | 540/310 |

Primary Examiner—Ernest G. Therkorn
Attorney, Agent, or Firm—H. G. Jackson

[57] ABSTRACT

A process for producing the compound [2S-(2α,3β,5α)]-3-methyl-7-oxo-3-(1H-1,2,3-triazol-1-yl-methyl)-4-thia-1-azabicyclo[3 2 0]-heptane-2-carboxylic acid, (4-nitrophenyl)methyl ester, 4,4-dioxide, which comprises reacting a solution of azidopenamsulfone, 4-methoxyphenol and vinylpropionate with a solution of bis(trimethylsilyl)acetamide and 4-methoxyphenol is toluene at 80°–100° C. for 18–30 hours followed by filtering the resulting solution and cooling the filtrate to 0°–10° C.

1 Claim, No Drawings

PROCESS FOR PRODUCING BETA-LACTAMASE INHIBITOR

SUMMARY OF THE INVENTION

This invention is concerned with an improved process for producing the intermediate [2S-(2α,3β,5α)]-3-methyl-7-oxo-3-(1H-1,2,3-triazol-1-ylmethyl)-4-thia-1=azabicyclo[3.2.0]heptane-2-carboxylic acid, (4-nitrophenyl)-methyl ester, 4,4-dioxide, having the structure

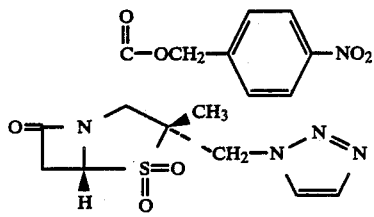

The improvement resides in an increased yield (60%) and purity (90%), the elimination of two steps in the heretofor known synthesis and allows isolation directly from the reaction mixture without resorting to chromatography.

The above described intermediate is then used to produce the biologically active β-lactamase inhibitor [2S-(2α,3β,5α,)]-3-methyl-7-oxo-3-(1H-1,2,3-triazol-1-ylmethyl)-4-thia-1-azabicyclo[3.2.0]heptane-2-carboxylic acid, 4,4-dioxide having the formula

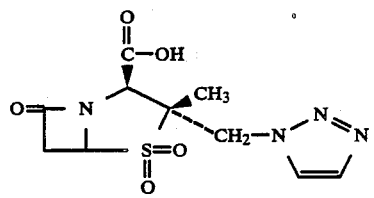

DESCRIPTION OF THE INVENTION

The process improvement which is the subject of this invention is described by the following reaction scheme an description:

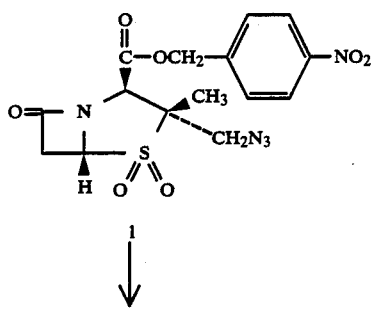

According to the above reaction azidopenamsulfone 1 is dissolved in vinyl propionate containing 4-methoxyphenol and this solution is reacted dropwise with a solution of bis(trimethylsilyl)acetamide and 4-methoxyphenol in toluene at 70°–180° C. followed by reaction at 95°–100° C. for about 24 hours and filtration and cooling to produce the intermediated [2S-(2α,3β,5α,)]-3-methyl-7-oxo-3-(1H-1,2,3-triazol-1-ylmethyl)-4-thia-1-azabicyclo[3.2.0]heptane-2-carboxylic acid, (4-nitrophenyl)methyl ester, 4,4-dioxide, 2 having 90% purity and in 60% yield.

The intermediate 2 is then hydrogenated over 5% palladium on carbon in ethyl acetate/water, containing sodium bicarbonate, followed by acidification with a mineral acid, giving the desired β-lactamase inhibitor 3.

EXAMPLE 1

[2S-(2α,3β,5α)]-3-Methyl-7-oxo=3=(1H-1,2,3-triazol-1-ylmethyl)-4-thia-1-azabicyclo[3.2.0]-heptane-2-carboxylic acid, (4-nitrophenyl)-methyl ester 4,4-dioxide An ethyl acetate solution containing 84 g of azidopenamsulfone was evaporated to dryness, then added to 1865 ml of vinyl propionate containing 4 g of 4-methoxyphenol and stirred for 1 hour. The solution was filtered and the filtrate added dropwise over 3.5 hours to a solution comprised of 1324 ml of toluene, 84 ml (66.8 g) of bis(trimethylsilyl)acetamide and 4 g of 4-methoxyphenol at 70°–80° C. When addition was complete the reaction temperature was raised to 95°–100° C. and maintained for 24 hours. The reaction was then cooled to room temperature, combined with 11 g of hydrous magnesium silicate, stirred for 20 minutes and then filtered through a bed of 33 g of hydrous magnesium silicate. The filtrate was rotoevaporated, collecting 2500 ml of distillate. The filtrate was stirred at room temperature for 12 hours, then cooled to 0°–5° C. for 2 hours and the resulting solid collected, washed with heptane and dried, giving 5 g of the desired intermediate with a purity of 90%.

We claim:

1. A process for producing the compound [2S-(2α,3β,5α)]-3-methyl-7-oxo-3-(1H-1,2,3-triazol-1-ylmethyl)-4-thia-1-azabicyclo[3.2.0]-heptane-2-carboxylic acid, (4-nitrophenyl)methyl ester, 4,4-dioxide, which comprises reacting a solution of azidopenamsulfone, 4-methoxyphenol and vinylpropionate with a solution of bis(trimethylsilyl)acetamide and 4-methoxyphenol in toluene at 80°–100° C. for 18–30 hours followed by filtering the resulting solution and cooling the filtrate to 0°–10° C.

* * * * *